United States Patent [19]

Geils

[11] 4,122,169

[45] Oct. 24, 1978

[54] ACTIVATED CARBON-SORBITAL COMPOSITION AND ADSORPTION-EXPULSION TREATMENT THEREWITH

[76] Inventor: John H. Geils, 180 Old Mill Rd., Greenwich, Conn. 06830

[21] Appl. No.: 680,853

[22] Filed: Apr. 27, 1976

[51] Int. Cl.$^2$ .............................................. A61K 33/44
[52] U.S. Cl. .................................................. 424/125
[58] Field of Search ....................................... 424/125

[56] References Cited

U.S. PATENT DOCUMENTS 3,917,821  11/1975  Manes .................................. 424/125

OTHER PUBLICATIONS

Liquid Oral Preparation . . . Sorbitol, Atlas Chem. Ind. Inc., 1962, pp. 6–8.

Primary Examiner—Jerome D. Goldberg
Attorney, Agent, or Firm—Dayton R. Stemple, Jr.

[57] ABSTRACT

A method and composition for removal of undesirable materials such as poisons from the gastrointestinal tract including the ingestion of a mixture of sorbitol and activated carbon whereby the activated carbon adsorbs the undesired material and carries it through the digestive tract, accelerated by the laxative action of sorbitol.

6 Claims, No Drawings

ACTIVATED CARBON-SORBITAL COMPOSITION AND ADSORPTION-EXPULSION TREATMENT THEREWITH

BACKGROUND OF INVENTION

This invention relates to new and useful improvements in a convenient, tasty composition of matter and method designed to remove undesirable materials from the gastrointestinal tract by a united adsorptive action and laxative action by combining activated carbon and sorbitol.

The highly adsorptive properties of activated carbon (particularly activated charcoal) are well known. Moreover, it has been used to remove noxious substances and gases from the gastrointestinal tract, to serve as an antidote, detoxicant and deflatulent. In fact, quantitative adsorption relationships can be worked out between activated carbon and various drugs or poisons including strychnine, digitalis, atropine, morphine, bichloride of mercury, arsenite, iodine, camphor, etc.

One difficulty, however, has been the introduction of the activated carbon, which is manufactured as a very fine powder, into the stomach because patients have difficulty in swallowing the powder or water slurry thereof. This had led to it being encapsulated, tableted and/or mixed with excipients and binders to avoid the powder. The problem generally encountered in mixing the activated carbon with other substances has been the masking of the adsorptive capacity of the carbon, thereby reducing same for the targeted undesired materials.

Sorbitol is a polyhydric alcohol having many properties of the sugars including water solubility and about 60% sweetness of sucrose. It is recognized as safe by the Food and Drug Administration by having been placed on the GRAS list. It is used as a sweetening agent, particularly for diabetic diets, and as a humectant to extend shelf life. It has a laxative action when consumed in large quantities (25 to 50 grams daily) which is believed related to its slow intestinal absorption.

OBJECTS OF INVENTION

It is an object of this invention to provide a method and composition to effectively and quickly remove undesirable materials from the gastrointestinal tract.

It is a further object to do so with a nontoxic composition that can be readily available to the public as an over the counter preparation.

It is another object to provide a highly adsorptive preparation that will be expelled quickly from the GI tract.

SUMMARY OF INVENTION

It has been found that a composition comprising activated carbon and sorbitol provides an excellent preparation for ease of administration, effective adsorption of many undesirable materials and the quick transport of same through the GI tract, of humans and animals, to defecation.

DETAILED DESCRIPTION

The dosage must provide sufficient activated carbon (usual dose for adults or children is 5 to 50 grams) to adsorb the particular undesired material. A preferred dosage is 70 g. of sorbitol solution (70%), i.e., 49 g. sorbitol and 21 g. $H_2O$, and 30 g. activated carbon, which is considered a good adsorbing dosage for most situations. Moreover, this ratio makes a good cream-like consistency and taste for the patient to ingest, and is self-preserving.

Obviously, U.S.P. grades of material should be used, for example, Norit brand activated carbon and Pfizer brand sorbitol.

Sorbitol is freely soluble in water up to 83% and a 65% solution is the minimum self-preserving solution. The carbon is, of course, insoluble. Other excipients may be added if desired for taste, consistency, etc., but generally the three ingredients here disclosed are sufficient and may be in the following ranges by weight:

| | |
|---|---|
| $H_2O$ | 10 to 30% |
| Sorbitol | 40 to 80% |
| Activated Carbon | 5 to 40% |

Since none of the materials are toxic, overdosage is of no concern except for the laxative effect and possible removal of desired materials from the GI tract.

I claim:

1. A composition of matter for removing undesirable materials from the gastrointestinal tract of humans or animals comprising 10 to 30% water, 40 to 80% sorbitol and 20 to 40% powdered activated carbon.

2. The composition of claim 1 comprising about 21% water, 49% sorbitol and 30% carbon, having a cream-like consistency.

3. A method for treating humans or animals to remove undesirable materials from the gastrointestinal tract that are adsorbable by activated carbon comprising oral ingestion by said humans or animals of an effective amount of the composition of claim 1.

4. A method for treating humans or animals to remove undesirable materials from the gastrointestinal tract that are adsorbable by activated carbon comprising oral ingestion by humans of the composition of claim 1 in sufficient amount to provide 5 to 50 grams of said carbon.

5. The method of claim 4 wherein said activated carbon is 5 to 50 grams, said sorbitol is 25 to 80 grams and said water is 7 to 35 grams.

6. The method of claim 4 wherein said activated carbon is about 30 grams, said sorbitol is about 49 grams and said water is about 21 grams.

* * * * *